United States Patent [19]

Schulze-Ganzlin et al.

[11] Patent Number: 4,995,062
[45] Date of Patent: * Feb. 19, 1991

[54] X-RAY DIAGNOSTICS INSTALLATION FOR PRODUCING PANORAMA TOMOGRAMS OF THE JAW OF A PATIENT

[75] Inventors: Ulrich Schulze-Ganzlin, Lorsch; Joachim Pfeiffer, Bensheim; Axel Schwotzer, Buettelborn, all of Fed. Rep. of Germany

[73] Assignee: Siemens Aktiengesellschaft, Berlin and Munich, Fed. Rep. of Germany

[*] Notice: The portion of the term of this patent subsequent to Oct. 31, 2006 has been disclaimed.

[21] Appl. No.: 386,603

[22] Filed: Jul. 31, 1989

[30] Foreign Application Priority Data

Aug. 12, 1988 [DE] Fed. Rep. of Germany ....... 3827474

[51] Int. Cl.⁵ ............................................. A61B 6/14
[52] U.S. Cl. ......................................... 378/22; 378/40
[58] Field of Search ................................... 378/21–27, 378/38–40

[56] References Cited

U.S. PATENT DOCUMENTS

| Re. 32,779 | 11/1988 | Kruger | 378/22 |
|---|---|---|---|
| 4,188,537 | 2/1980 | Franke | 250/416 |
| 4,442,534 | 4/1984 | Haendle et al. | 378/21 |
| 4,823,369 | 4/1989 | Guenther et al. | |
| 4,878,234 | 10/1989 | Pfeiffer et al. | |

FOREIGN PATENT DOCUMENTS 0138625 4/1985 European Pat. Off. .

Primary Examiner—Carolyn E. Fields
Assistant Examiner—David P. Porta
Attorney, Agent, or Firm—Hill, Van Santen, Steadman & Simpson

[57] ABSTRACT

A dental x-ray diagnostics installation for producing panorama tomograms of the jaw of a patient has clocked CCD sensors which generate electrical signals proportional to the radiation intensity thereon, and which are operated at a speed to simulate a moving x-ray film. For the purpose of simultaneously acquiring exposures of a number of different jaw slices at different depths of field during one exposure, at least some of the CCD columns are driven with different clock frequencies by separate clock inputs.

8 Claims, 3 Drawing Sheets

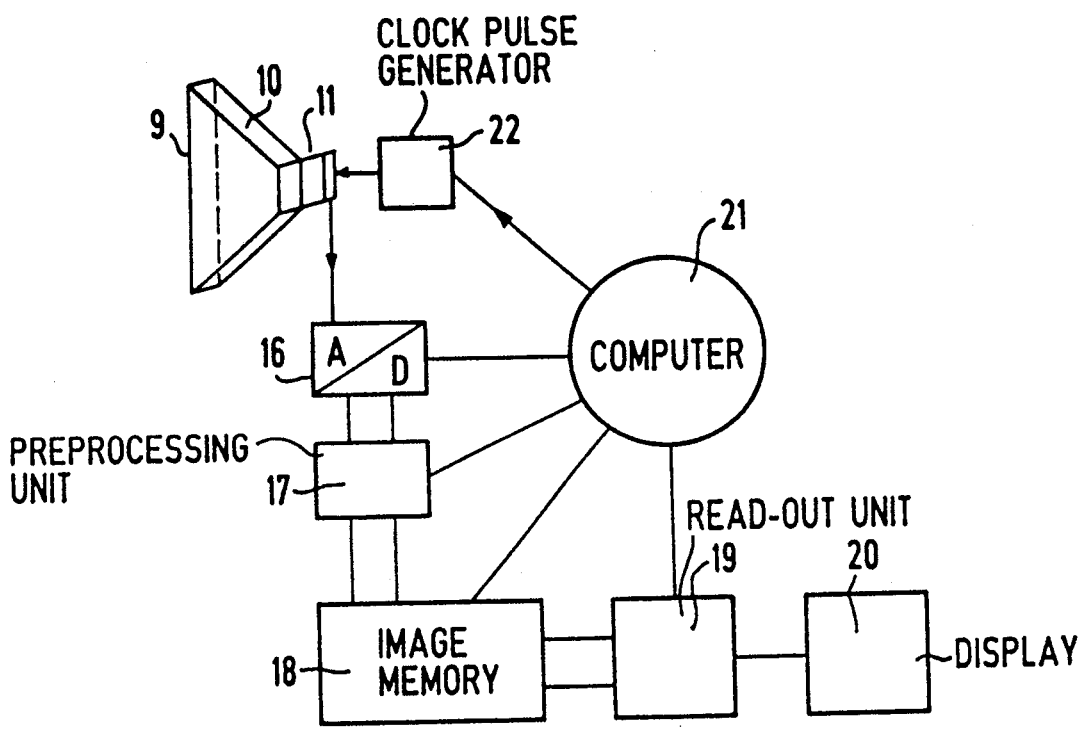
FIG 4
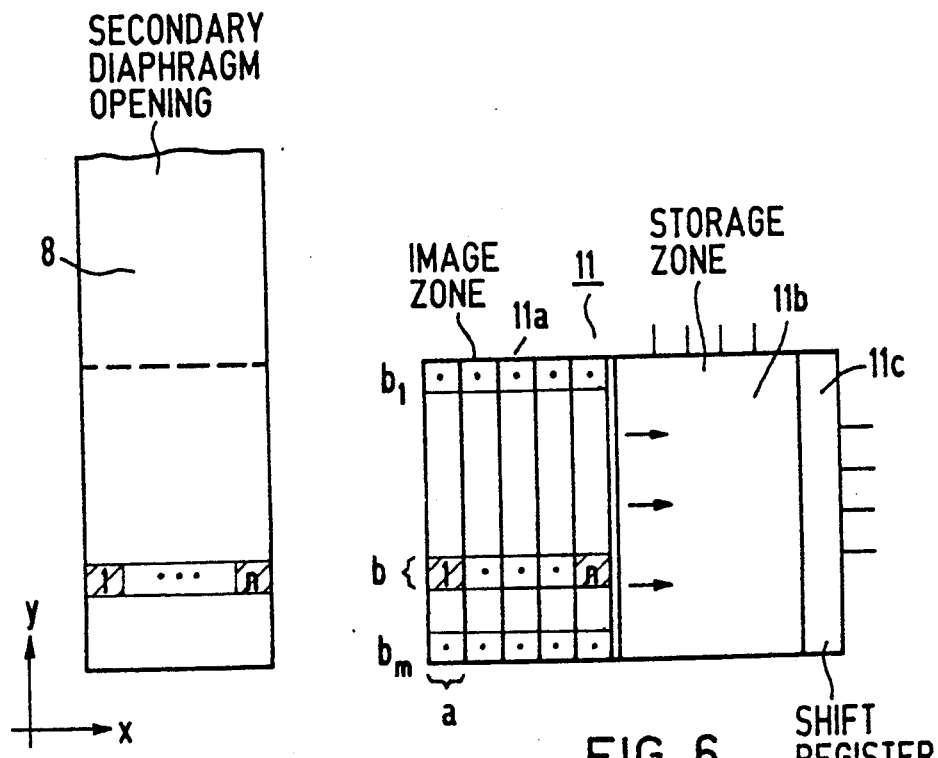
FIG 5
FIG 6

X-RAY DIAGNOSTICS INSTALLATION FOR PRODUCING PANORAMA TOMOGRAMS OF THE JAW OF A PATIENT

BACKGROUND OF THE INVENTION

1. Field of the Invention

The present invention is directed to a dental x-ray diagnostics installation for producing panorama tomograms of the jaw of a patient, and in particular to such an installation wherein the radiation intensity is measured by clocked CCD sensors which are operated at a clock frequency to simulate a moving x-ray film.

2. Related Patent and Application

A dental x-ray diagnostics installation for producing panorama tomograms of the jaw of a patient, wherein the moving x-ray film used in previous installations of this type is replaced by a clocked CCD sensor arrangement operated to simulate the moving film, is disclosed in U.S. Pat. No. 4,823,369. The details of operation of the CCD sensor are disclosed in U.S. Pat. No. 4,878,234, and which is assigned to the same assignee as the present application.

The dental x-ray installation disclosed in the above differs from conventional panorama tomogram exposure equipment in that the x-ray film, which is moved behind the secondary diaphragm in conventional systems, is replaced by a stationary CCD sensor arrangement which is driven with a clock generator so that the charge images which are obtained are entered into a storage zone at a clock frequency to simulate the same speed at which the conventional x-ray film is moved relative to the secondary diaphragm. The charge images are then clocked out line-by-line by a shift register. The clock frequency $f_T$ is selected according to the relationship:

$$f_T = v/(n_x \cdot a)$$

wherein v is the conventional film speed, $n_x$ is the imaging relationship of the image-transmitting system, and a is the line spacing.

SUMMARY OF THE INVENTION

It is an object of the present invention to provide, in a clocked CCD sensor dental x-ray panorama tomographic installation, the capability of simultaneously acquiring a plurality of tomograms during one exposure, with the tomograms being selectable within certain limits.

It is a further object of the present invention to provide such an installation wherein accurate tomograms of slices which lie on a curved path, rather than in one plane, can be obtained, for example, tomograms of teeth disposed at an angle in the jaw.

These and other objects ar achieved in accordance with the principles of the present invention in an x-ray diagnostics installation having a clocked CCD sensor arrangement for recording the x-radiation intensity has at least some of the CCD columns driven at different clock frequencies via separate clock inputs, thereby permitting a plurality of slices to be simultaneously acquired during the execution of a single exposure. Moreover, each slice can be freely defined within certain limits.

The different clock drives need not be used to clock the entire CCD sensor (or the entire CCD sensor arrangement, if more than one CCD sensor is used); the differing clock drive can be used to drive only specific regions of the CCD sensor, or only selected ones of the sensors comprising a CCD sensor arrangement. The clock frequencies used to drive different groups of columns can be divided such that the slice being recorded assumes a curved path, so that teeth lying at an angle within the jaw can be sharply imaged.

The depth of field of the acquired image can be varied by varying the width of the image zone within the CCD sensor by rendering some of the lines of the sensor passive.

DESCRIPTION OF THE DRAWINGS

FIG. 4 is a schematic block diagram of signal processing components for the dental installation shown in FIG. 1.

FIG. 5 is a front view of the opening of the secondary diaphragm in the installation of FIG. 1 showing a segment to explain the operation of the apparatus.

FIG. 6 is a plane view of a CCD sensor used in the installation of FIG. 1 segmented to explain the operation of the apparatus.

DESCRIPTION OF THE PREFERRED EMBODIMENTS

Figure 1:
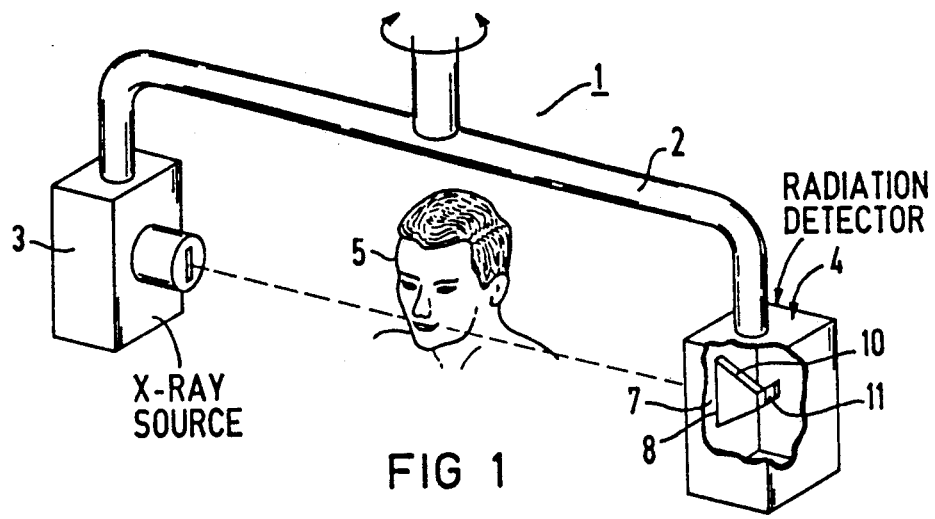
FIG. 1 is a perspective view of an x-ray diagnostics installation wherein moving x-ray film is replaced by a CCD sensor.

The x-ray diagnostics installation shown in FIGS. 1-4 is as disclosed in the aforementioned U.S. Pat. No. 4,283,369 and the CCD sensor structure and operation shown in FIGS. 5 and 6 are as disclosed in the aforementioned U.S. Pat. No. 4,878,234 with some details having been added to FIG. 6 to explain the principles of the present invention. The installation includes a rotary unit generally referenced 1, consisting of an x-ray source 3 and a secondary diaphragm 7, with a detector arrangement 4 attached thereto, mounted at opposite ends of a carrier 2. The rotary unit 1 can be rotated around the head of a patient 5 in a known manner, as indicated by the arrow. Adjustment and control devices for rotating the unit 1 to generate a panorama tomogram of the jaw of the patient 5 are known to those skilled in the art, and need not be further described. It need only be noted that the head of the patient 5 is fixed in position with a mount (not shown) during an exposure, and the rotary unit 1 moves with a defined speed around the patient 5 given a prescribed exposure time. This movement is undertaken such that the x-ray emitted by the x-ray source incident on the jaw of the patient 5 at substantially a right angle, and a substantially constant distance between the jaw and the detector 4 is maintained.

The secondary diaphragm 7 has a slot-like opening 8 having dimensions of, for example, 5×125 mm. The opening 8 is followed by means for converting the x-rays into visible light radiation. In the exemplary embodiment, a scintillator layer 9 having substantially the same dimensions as the opening 8 is provided for this purpose in the plane of the opening 8. The scintillator layer 9 is followed by an image transmission or coupling element 10, such as fiber optics, which reduces the format of the secondary diaphragm opening 8 to the format of the image zone of a CCD sensor 11. The image zone of the CCD sensor 11 has dimensions of, for example, 8×8 mm.

The CCD sensor 11 is of the type having an image zone 11a and a storage zone 11b disposes spatially separated on a chip, and having a shift register 11c coupled to the storage zone 11b. It is also possible, however, to use a CCD sensor of the type wherein the image and storage zones are disposed together within a chip.

Figure 2:
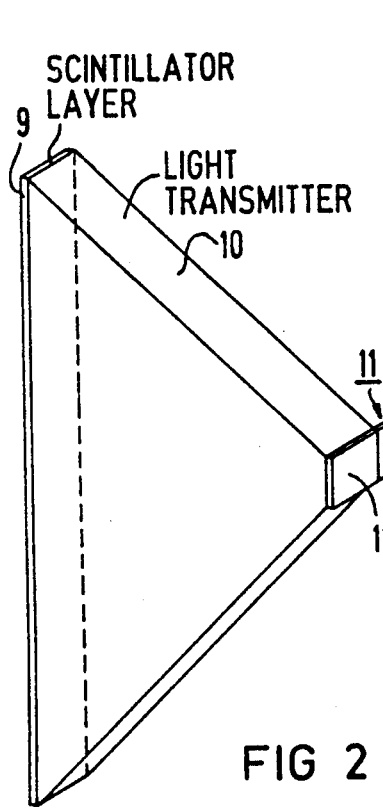
FIG. 2 is a perspective view of a detector and sensor arrangement using a single CCD sensor.
Figure 3:
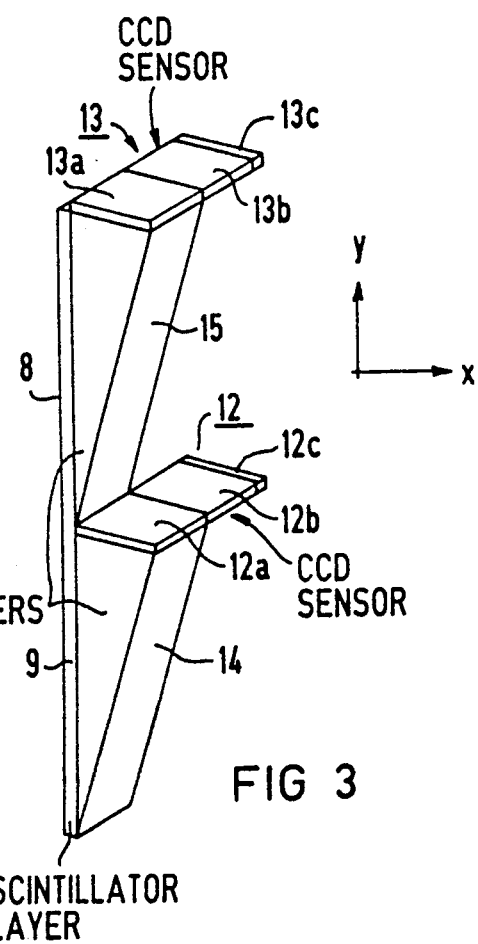
FIG. 3 is a perspective view of a detector and sensor arrangement using more than one CCD sensor.

To simplify the following description, it shall be assumed that the entire extent of the opening 8 in the secondary diaphragm 11 is imaged onto the surface of a single CCD sensor, as shown in FIG. 2. It is possible, however, to provide a plurality of such CCD sensors to cover the entirety of the opening 8, as shown in the embodiment of FIG. 3. In the embodiment of FIG. 3, two CCD sensors 12 and 13 are disposed at substantially a right angle relative to the plane of the opening 8, and two fiber optic elements 14 and 15 are provided as the transmission or coupling elements. The individual CCD sensors are of the same type as shown in FIG. 2, that is, with a storage zone spatially separated from an image zone, with a following shift register.

Processing of the electronic signals from the sensor 11 is undertaken using the components shown in Figure 4. The output of the shift register 11c is supplied to an analog-to-digital converter 16, which is followed by a digital image processing system including a pre-processing unit 17, an image memory 18, an image read-out unit 19, a display 20, a computer 21 and a clocks pulse generator 22. Image data in the form of voltage signals generated by charge proportional to the x-ray intensity are supplied at the output of the shift register 11c. These voltages are converted to digital signals in the converter 16. These digital values can then either be directly entered and stored in the image memory 18, or can be entered and stored in the image memory 18 after pre-processing in the unit 17. The computer 21 provides control (read-out) instructions required for this purpose through the clock pulse generator 22.

Direct entry of signals from the analog-to-digital converter 16 into the image memory 18 is preferable if the image memory 18 has a sufficiently large memory capacity, which can be justified given the constraints of cost and physical size. If direct entry is undertaken, the data are stored only during rotation of the rotary unit 1 which is necessary to complete an exposure, and after the conclusion of this exposure the data are processed, i.e., are added to generate a tomogram of the desired slice of the patient's jaw. Even though a relatively large amount of data must be processed for this purpose, this method has the advantage that a subsequent visual representation of a plurality of different slices is possible.

If, however, it is not economically justifiable to provide an image memory 18 having such a large memory capacity, the pre-processing unit 17 may be interposed between the converter 16 and the image memory 18, as indicated with dashed lines in FIG. 4. The pre-processing unit 17 includes an intermediate memory and a signal processor, by means of which the digital data from the converter 16 are added as a function of time based on a control instruction from the computer 21. This addition is undertaken to generate a tomogram of a desired slice of the patient's jaw. The processed data are subsequently forwarded to the image memory 18. An image memory 18 having a lower memory capacity can thus be used if the pre-processing unit 17 is present. If the preprocessing unit 17 is used, however, the slice or tomograph position (i.e., depth) is fixed, so that the slice position can not be varied within certain limits, as would be possible without the pre-processing unit 17, wherein the image data are not combined to form a tomogram until after a complete exposure.

A compromise solution is possible, however, wherein a plurality of adjacent image columns (i.e., data sets corresponding to successive positions of the secondary diaphragm 7, and thus of the opening 8 therein) are added as a function of time before storing this data, and the subsequent addition of these sum columns to form an image column is not undertaken until after storing the data. Using this method, the pre-processing unit 17 is not required to add all of the data, but only the data for a few adjacent columns. The data for these few columns are added as a function of time under the control of the computer 21, and are then forwarded to the image memory 18

The creation of an image in the above-described apparatus shall be discussed below with reference to FIGS. 5 and 6.

The patient 5 is transradiated by a rectangular slot-shaped x-ray beam defined by a primary diaphragm (not shown) situated in the x-ray source 3. The radiation passes through the opening 8 of the secondary diaphragm 7 and is incident on the scintillator layer 9, wherein the x-radiation is converted into light radiation, to be registered by the CCD sensor 11. The signals registered by the CCD sensor 11 are proportional to the radiation intensity of the x-radiation attenuated by the patient 5.

In conventional tomographic techniques, an x-ray film to be exposed is moved at a defined speed behind the opening 8 of the secondary diaphragm 7, with the speed of film movement being a factor which defines the position (depth) of the tomographic slice. The position of the tomographic slice can thus be modified by varying the film speed. As described below, in the apparatus disclosed herein the x-ray film is replaced by an electronic detector arrangement, and the signals generated by the electronic detector arrangement are processed in a manner to generate a panorama tomogram corresponding to a tomogram produced using conventional moving film technology, but which can be reproduced on a television monitor.

The relationship between the opening 8 and the image zone 11a of the CCD sensor 11 shall first be described with reference to FIGS. 5 and 6. It is assumed that the opening 8 is imaged on the image zone of one or more such CCD sensors. The imaging relationship in the x-direction, i.e., perpendicular to the longitudinal extent of the opening 8, is defined by the ratio $1:n_x$, and by the ratio $1:n_y$ in the y-direction. Because the opening 8 has a width of about 5 mm, and currently available CCD sensors have an image zone width of about 5 mm, and currently available CCD sensors have an image zone width of 8 mm, $n_x=1$ is applicable in the present context. Dependent on the number and size of image sensors employed, the imaging scale $n_y$ is the longitudinal (y) slot direction can be between 1 and about 20.

A picture element (pixel) on the CCD image zone surface having the dimensions a×b (a=row or line spacing, b=column spacing) corresponds to a pixel of $(n_x a) \times (n_y a)$ in the plane of the opening 8. In the simplified overview of FIGS. 5 and 6, 1 through n correspond to charge pixels in the CCD sensor, and also identify pixels in the direction of the longitudinal extent of the secondary opening 8. Accordingly, a line in this longitudinal direction of the secondary opening 8 is imaged on a CCD row or line.

By the application of clock pulses from the clock pulse generator 22, a charge image is transferred from the image zone 11a into the storage zone 11b, and is then read-out from the storage zone 11b via the shift register 11c, for supply to the analog-to-digital converter 16. During normal operation, i.e., in the standard clock sequence of a CCD sensor, the image integration time is approximately 20 ms. The image is clocked into the storage zone 11b in accord therewith. For this purpose, the same number of clock pulses as lines or rows of the CCd sensor is needed. Based on a CCD sensor type having 300 lines, and a clock period of 2 μs, the image zone 11a is thus emptied after about 0.6 ms, and can then immediately accept a new image. In conventional tomographic technology, the x-ray film is moved behind the secondary diaphragm opening at a defined speed so that the image data defined by the secondary opening are integrated over a defined time span during the movement of the film. This integration of the image data is electronically simulated in the present apparatus by clocking the charge image, generated by the action of the light radiation from the scintillator layer 9 on the surface of the CCD sensor 11, out of the image zone 11a into the storage zone 11b in a defined clock sequence, and then clocking the stored image out of the storage zone 11b line-by-line via the shift register 11c. The clock sequence is selected such that the charge image, referenced to the plane of the secondary opening 8, has the same speed in the x-direction which a moving x-ray film would have in conventional tomographic technology. The clock frequency $f_T$ thus has the following relationship to the equivalent speed v of a moving film:

$$F_t v/(n_x \cdot a)$$

wherein $f_T$ is the number of lines per second and $(n_x \cdot a)$ is the CCD line spacing referenced to the plane of the secondary opening 8. Given a typical film speed of 30 mm/s and a line spacing of 20 μm, and based on an imaging ratio of 1:1 in the x-direction, a clock frequency of 1500 Hz results.

Further details of the procedure for image integration can be found in the aforementioned U.S. Pat. No. 4,878,234.

As mentioned above, the use of a storage zone in the CCD sensor is not absolutely necessary; the charge may be transferred from the image zone directly into the shift register line-by-line, and then clocked out from the shift register. An additional charge transfer step can thus be avoided.

For explaining the principles of the present invention, it is assumed that the CCD sensor 11 shown in FIG. 6 is subdivided into columns $b_1$ through $b_m$. As previously explained, a charge image corresponding to and exposed region on a conventionally irradiated x-ray film is produced by integration and by transferring the charges in the image zone 11a. The charges are shifted from one CCD line to the next column-by-column, and are clocked out into the storage 11b, or directly into a shift register 11c. The speed with which this transfer ensues is prescribed by the shift clock frequency. A sharply imaged sliced will be obtained if this frequency f corresponds to the following relationship:

$$f = (v/a)(d/(1-d))$$

wherein d is the distance of the film from the subject, 1 is the distance of the film from the radiation source, v is the speed of the radiation source perpendicular to the subject, a is the CCD line width, and f is the clock frequency.

The product (a·f) corresponds to the film speed in conventional x-ray exposure technology.

Figure 7:
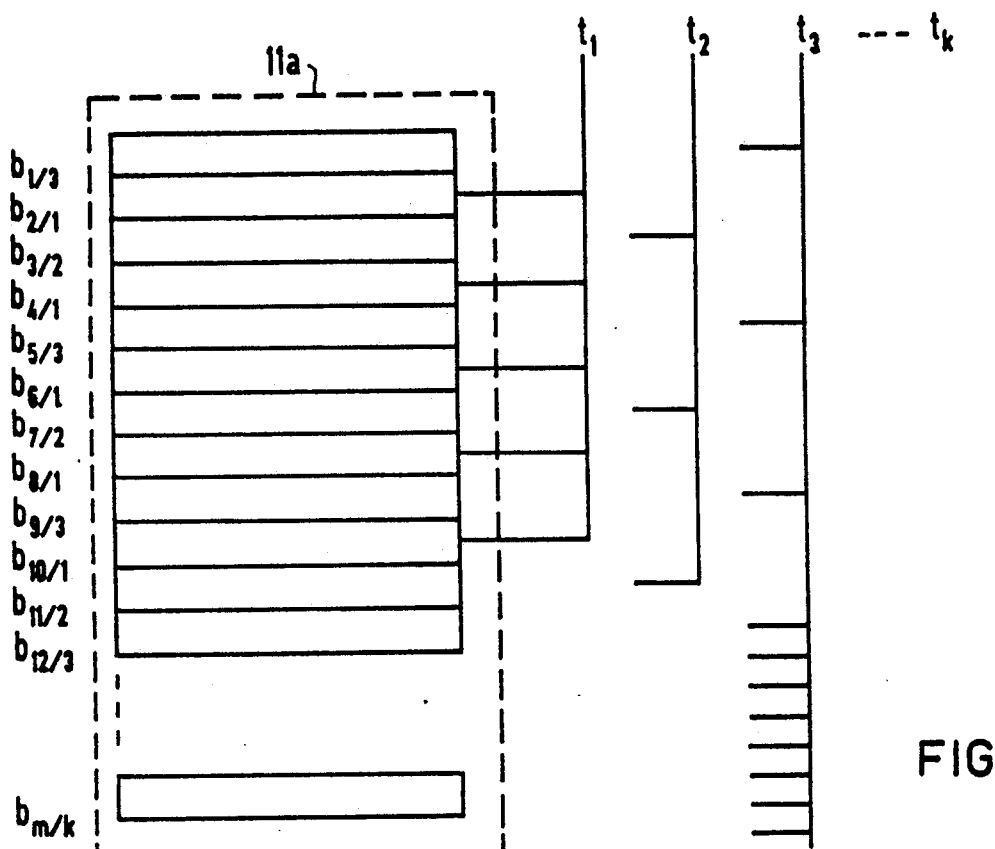
FIG. 7 is a schematic illustration for explaining the drive of columns in a CCD sensor as shown in FIGS. 5 and 6 using differing clock frequencies in accordance with the principles of the present invention.

As shown in FIG. 7, some of the CCD columns $b_1$ through $b_m$ are driven with different clock frequencies $t_1$ through $t_k$. Each clock frequency corresponds to an exposure. The clock drive can be uniformly distributed over the entire CCD sensor, however, it is advantageous to concentrate the different drive of the columns at specific surface regions of the CCD sensor (or specific regions of the secondary diaphragm slot) if a plurality of CCD sensor elements cover the secondary slot. Such a concentration on the specific surface regions can be used to obtain a plurality of tomograms corresponding to respectively different jaw slices within an imaging region. The generation of a plurality of tomograms will result in a slight reduction in the image resolution in comparison to the generation of one tomogram corresponding to the a single slice. Therefore the region wherein the reduction in image resolution occurs due to the generation of a plurality of tomograms can be limited, with the remainder of the panorama tomogram having normal resolution.

FIG. 7 shows such a concentration at the upper surface section of the CCD sensor 11a. In this embodiment, the columns $b_2$, $b_4$, $b_6$, $b_8$ and $b_{10}$ are driven with the clock frequency $t_1$, the columns $b_3$, $b_7$ and $b_{11}$ are driven with the clock frequency $t_2$, and the columns $b_1$, $b_5$, $b_9$ and $b_{12}$, and any further columns, are driven with the clock frequency $t_3$. This means that the columns in the upper section of the CCD sensor are driven with three different clock frequencies corresponding to different slices, whereas the CCD sensor is driven with only one clock frequency beginning with the 12th column. In the embodiment of FIG. 7, three different slices corresponding to the clock frequencies $t_1$, $t_2$ and $t_3$ can thus be acquired in the upper image section, whereas only one slice, namely the slice corresponding to the clock frequency $t_3$, is imaged in the lower image section.

The columns driven with the same clock frequency are preferably combined in groups, however, it is possible to drive each column individually. Each column has a corresponding clock input which, as shown in FIG. 4, is connected to the clock generator 22.

The clock frequencies $t_1$ through $t_k$ can be preferably divided so that the curved slice, rather than a planar slice, of the jaw is acquired. The computer 21 and the image processing unit 17 can portray all desired slices independently of each other, and further, intermediate slices can be calculated. A plurality of slices may also be combined into one slice having a greater range of depth of field.

Variation of the range of the depth of field can be achieved by varying the width of the active sensor surface. In accordance with the principles of the present invention, the width of a column in the CCD sensor can be "artificially" influenced during an exposure by rendering passive those CCD lines which lie at the edge of an image zone. The passivation or separating of lines can be achieved by dissipating charges into the substrate (ground) of the CCD sensor. Such an electrical decoupling of the charges can be preferably done by integrating analog switches on the CCD sensor. These switches are externally activated by corresponding signal lines. The active CCD sensor surface can be influenced by appropriate activation, with a larger active sensor surface corresponding to a smaller range of depth of field.

Figure 8:
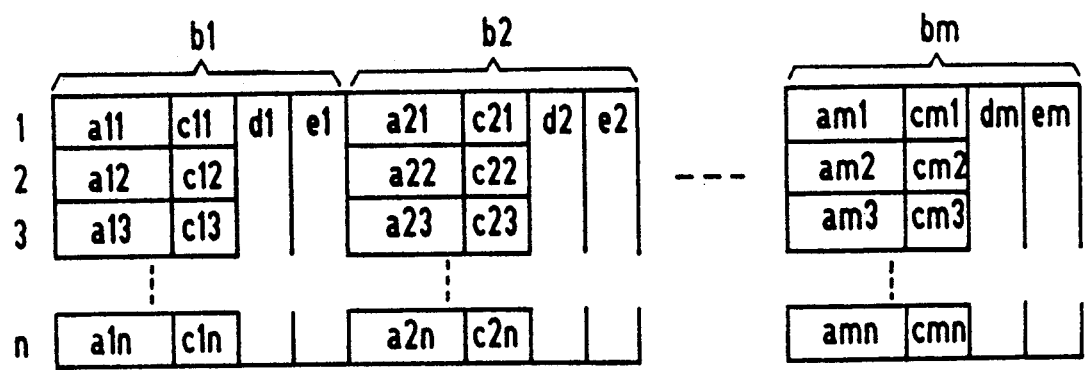
FIGS. 8, 9 and 10 are schematic illustrations showing charge transfer in a CCD sensor with columns driven at different clock frequencies in accordance with the principles of the present invention.
Figure 9:
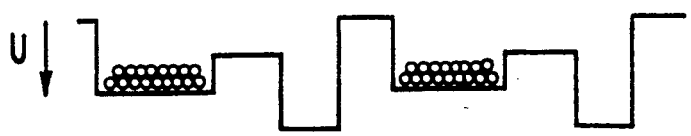
Figure 10:
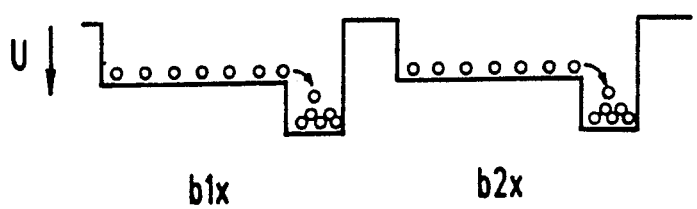

On possibility for decoupling charges is described in FIGS. 8 through 10. This technique can be used with a CCD sensor having a separate image zone and storage zone, or with a CCD sensor having no storage zone.

FIG. 8 schematically shows the arrangement of the photo-sensitive cells and electrodes of a CCD sensor. It is assumed that every pixel of a CCD sensor is composed of four regions. These regions are:

the photo-sensitive cells $a_{11}, a_{12}, a_{13} \ldots a_{1n}$, which are shown under one another in each column $b_1, b_2 \ldots b_m$ in the illustration for n lines;

the inhibiting electrodes $c_{11}, c_{12}, c_{13} \ldots c_{1n}$ for each cell having terminals (not shown) for controlling the decoupling;

the potential wells $d_1, d_2 \ldots d_m$ into which the charges are "extracted" after decoupling and are conducted to ground (i.e., the substrate of the CCD sensor); and the separating zones $e_1, e_2 \ldots e_n$ between the individual columns, $b_1, b_2 \ldots b_m$.

As shown in FIGS. 9 and 10, the four regions are at four different voltage potentials U, with the points of the arrows in FIGS. 9 and 10 indicating a higher voltage potential.

Normally the charge flows line-by-line (lines 1, 2 ... n) from $a_{11}, a_{12} \ldots a_{1n}$ to the image storage zone, or directly to the shift register if an image storage zone is not present. The distribution of the voltage potentials for these four regions is shown in FIG. 9 in this condition.

When the inhibiting electrode is activated at a specific location, for example, at $c_{13}$, this being done by a signal supplied thereto via a corresponding terminal, then all charge from $a_{11}$ through $a_{13}$ falls into the potential well $d_1$, resulting in this charge being quenched. This condition is schematically shown in FIG. 10.

By selectively driving specific inhibiting electrodes, the charge transfer to a specific location of the image plane can be interrupted, and the range of the depth of field can thereby be varied.

Although modifications and changes may be suggested by those skilled in the art, it is the intention of the inventors to embody within the patent warranted hereon all changes and modifications as reasonably and properly come within the scope of the their contribution to the art.

We claim as our invention:

1. A dental x-ray diagnostics installation for producing panorama tomograms of the jaw of a patient which simulate tomograms obtained by moving x-ray sensitive film behind and past a diaphragm opening at a selected film moving speed, comprising:

radiator means for generating x-radiation;

detector means for converting x-radiation incident thereon into corresponding light radiation;

a secondary diaphragm disposed in front of said detector means having a diaphragm opening which limits said x-radiation incident on said detector means;

means for supporting said radiator means and said detector means, with said secondary diaphragm, on opposite sides of a patient's preceding jaw and for rotating said radiator means, said secondary diaphragm and said detector means such that x-radiation attenuated by said jaw passes through said secondary diaphragm and is incident on said detector means;

CCD sensor means on which said light radiation is incident for converting said light radiation into electrical signals, said CCD sensor means having an image zone with a plurality of lines and columns in each of which charge is generated corresponding to a portion of said light radiation incident, said charge forming a charge image;

storage means into which charge from said image zone of said CCD sensor means is transferred for storing said charge image in rows and columns;

means for reading out said storage means; and clock means connected to said CCD sensor means for generating clock pulses at a clock frequency to control the speed of transfer of charge from said lines to said storage means, and connected to said means for reading out to control the speed of reading out of said charge image from said storage means, said clock means generating said clock pulses at a clock frequency to transfer charge line-by-line from said image zone to said storage means and to read out said charge image from said storage means line-by-line at a speed selected to simulate said moving film speed, and for generating further clock pulses for driving different columns of said CCD sensor means at different clock frequencies via separate clock inputs respectively connected to said different columns to simultaneously obtain a plurality of tomograms corresponding to respective slices at different depths of said jaw.

2. A dental x-ray diagnostics installation as claimed in claim 1, wherein said storage means comprises a storage zone in said CCD sensor means.

3. A dental x-ray diagnostics installation as claimed in claim 1, wherein said storage means comprises a shift register connected to said CCD sensor means.

4. A dental x-ray diagnostics installation as claimed in claim 1, wherein said clock means is a means for individually driving respectively different columns of said CCD sensor means at different clock frequencies via individual, separate clock inputs respectively connected to said individual different columns.

5. A dental x-ray diagnostics installation as claimed in claim 1, wherein said clock means is a clock means for driving different groups of columns of said CCD sensor means at different clock frequencies via separate clock inputs respectively connected to all columns in each group of columns.

6. A dental x-ray diagnostics installation as claimed in claim 1, wherein said clock means is a clock means for driving different columns of said CCD sensor means at different clock frequencies via separate clock inputs respectively connected to said different columns with said clock frequencies being divisible to generate a tomogram of a curved slice of said jaw of said patient.

7. A dental x-ray diagnostics installation as claimed in claim 1, further comprising means for varying the width of said image zone of said CCD sensor means, to vary the depth of field of the resulting tomogram, by electrically decoupling charges generated in said CCD sensor means at edges of said image zone.

8. A dental x-ray diagnostics installation as claimed in claim 7, wherein said means for varying the width of said image zone comprises a plurality of integrated normally open analog switches respectively connected to said columns of said CCD sensor means and to ground, and means for selectively closing individual ones of said analog switches so that charge in a column connected to a closed analog switch is conducted to ground instead of being transferred to said storage means.

* * * * *